US010062592B2

(12) United States Patent
Kawasaki et al.

(10) Patent No.: US 10,062,592 B2
(45) Date of Patent: Aug. 28, 2018

(54) SUBSTRATE PROCESSING APPARATUS

(71) Applicant: HITACHI KOKUSAI ELECTRIC INC., Tokyo (JP)

(72) Inventors: Junichi Kawasaki, Toyama (JP); Hajime Abiko, Toyama (JP)

(73) Assignee: HITACHI KOKUSAI ELECTRIC INC., Tokyo (JP)

(*) Notice: Subject to any disclaimer, the term of this patent is extended or adjusted under 35 U.S.C. 154(b) by 0 days.

(21) Appl. No.: 15/418,796

(22) Filed: Jan. 30, 2017

(65) Prior Publication Data

US 2017/0140963 A1 May 18, 2017

Related U.S. Application Data

(63) Continuation of application No. PCT/JP2015/071486, filed on Jul. 29, 2015.

(30) Foreign Application Priority Data

Jul. 30, 2014 (JP) .................................. 2014-154756

(51) Int. Cl.
H01L 21/67 (2006.01)
H01L 21/677 (2006.01)
H01L 21/02 (2006.01)
G01N 21/95 (2006.01)

(52) U.S. Cl.
CPC ... H01L 21/67288 (2013.01); G01N 21/9501 (2013.01); H01L 21/0226 (2013.01); H01L 21/67703 (2013.01); G01N 2201/13 (2013.01)

(58) Field of Classification Search
USPC ........................................................ 700/226
See application file for complete search history.

(56) References Cited

U.S. PATENT DOCUMENTS

| 5,540,098 A | 7/1996 | Dhsawa |
| 7,751,922 B2 | 7/2010 | Hirano et al. |
| 2008/0127467 A1* | 6/2008 | Hirano ............. H01L 21/67109 29/25.01 |
| 2009/0114150 A1* | 5/2009 | Yoneda ............. H01L 21/67253 118/696 |

FOREIGN PATENT DOCUMENTS

| JP | 06-244268 A | 9/1994 |
| JP | 4503088 B2 | 7/2010 |
| JP | 4555302 B2 | 9/2010 |

* cited by examiner

*Primary Examiner* — Kyle O Logan
(74) *Attorney, Agent, or Firm* — Volpe and Koenig, P.C.

(57) ABSTRACT

A substrate processing apparatus includes a substrate retaining mechanism; a detecting unit detecting a placed state of the substrate retained by the substrate retaining mechanism; a first determination unit comparing detection data of the substrate obtained by the detecting unit with master data that is a reference to determine if the detection data is within a first allowed value; a confirmation unit confirming substrate type; a second determination unit comparing the detection data of the substrate with the master data to determine if the detection data is within a second allowed value; and a transfer control unit controlling the substrate retaining mechanism depending on a determination result of the second determination unit when substrate type is confirmed as a predetermined type by the confirmation unit when it is determined that the detection data is not within the first allowed value as determined by the first determination unit.

14 Claims, 5 Drawing Sheets

SUBSTRATE PROCESSING APPARATUS

TECHNICAL FIELD

The present invention relates to a substrate processing apparatus capable of performing treatment such as thin film formation, oxidation, impurity diffusion, and annealing, on a substrate (such as silicon wafer, glass substrate), and particularly, detecting a deformation of the substrate or crack in the substrate; a method of transferring a substrate; a method of manufacturing a semiconductor device; and a recording medium storing a state detection program.

BACKGROUND

As a processing apparatus configured to process a substrate, there is a batch type substrate processing apparatus including a vertical-type reaction furnace, a boat that is a substrate retaining mechanism configured to retain a predetermined number of processing substrates (hereinafter referred to as wafers) in a horizontal position in multiple stages, and a substrate transfer machine configured to transfer the wafers into the boat, and processing the wafers in the reaction furnace while the wafers are retained in the boat.

Conventionally, a wafer crack detection mechanism is installed for detecting an abnormality of the wafer in the substrate processing apparatus so that substrate processing is not continued in a state in which the abnormality occurs in the wafer when the abnormality such as a crack, warp, or misalignment occurs in the wafer due to thermal stress during heating in the reaction furnace, and during cooling when the wafer is taken out from the reaction furnace.

As disclosed in WO2005/31851 A, in a wafer crack detection function, a photoelectric sensor arranged in a horizontal direction at a position at which a wafer end face is detected is moved at a constant speed in a vertical direction with respect to a boat to which the wafer is transferred, and a state of the wafer is determined from a change in the amount of light during the movement.

In addition, according to JP 2013-212723 A, the change of the amount of light at a position exceeding the threshold value (slightly low) and a position being out of the threshold value (slightly high) with respect to a prescribed threshold value and a position in which the value becomes maximum (peak) are obtained and used for determination. As for a reference value to be used for determination of a wafer state, data of the slightly high, slightly low, and peak of each slot on the boat are obtained in a state in which a normal wafer is arranged, and are retained by a system as master data. When wafer crack detection is executed, the data are obtained of the slightly high, slightly low, and peak of each slot, and differences from the master data are calculated. When the difference from the master data exceeds an allowed value set in the system, it is determined that there is the abnormality, and it becomes a wafer abnormality detection state. Here, the allowed value of the difference from the master data is common in all slots, and a product wafer is used as a reference.

Further, there is a substrate processing apparatus in which a ring-shaped retaining member is mounted on the boat, and the wafer is placed on the retaining member in order to improve process performance condition. For example, according to JP 2013-212723 A, a function is described of detecting in advance a deformation or misalignment to the retaining member, in order to solve a problem that the wafer crack detection mechanism cannot be used, since the retaining member exists on the optical axis of the wafer crack detection mechanism, and the retaining member affects the waveform of the amount of light, in a state in which the retaining member is mounted on the boat.

Currently, it is necessary to strictly determine distortion for the product wafer. On the other hand, a dummy wafer is required to be used repeatedly even when some distortion or warp. Here, even in JP 2013-212723 A, it is disclosed that the allowed value for other wafers including the dummy wafer can be set on the basis of the product wafer. However, content of JP 2013-212723 A does not sufficiently respond to a solution of the above problem, the solution improving an apparatus operation rate by repeatedly using the dummy wafer and extending a replacement cycle of the dummy wafer.

SUMMARY OF INVENTION

An object of the present invention is to enable individual setting of the allowed value that is used for determination of abnormality detection by the substrate type, in substrate crack detection in various substrates, and to enable processing continuation by allowing a deformation due to continuous use of the dummy substrate.

According to an aspect of the present invention, a configuration is provided including: a substrate retaining mechanism retaining a substrate; a detecting unit configured to detect a placed state of the substrate retained by the substrate retaining mechanism; a first determination unit configured to compare detection data of the substrate obtained by the detecting unit with master data that is a reference and is obtained beforehand to determine whether or not the detection data of the substrate is within a first allowed value; a confirmation unit configured to confirm a type of the substrate; a second determination unit configured to compare the detection data of the substrate with the master data to determine whether or not the detection data is within a second allowed value; and a transfer control unit configured to control the substrate retaining mechanism depending on a determination result of the second determination unit when it is confirmed that a type of the substrate is a predetermined type by the confirmation unit when it is determined that the detection data is not within the first allowed value as a determination result of the first determination unit.

According to the present invention, abnormality detection can be determined in different ranges for substrate types in substrate crack processing, and the dummy substrate can be reused to the limit.

DESCRIPTION OF EMBODIMENT

Hereinafter, an embodiment of the present invention will be described with reference to the drawings.

Figure 1:
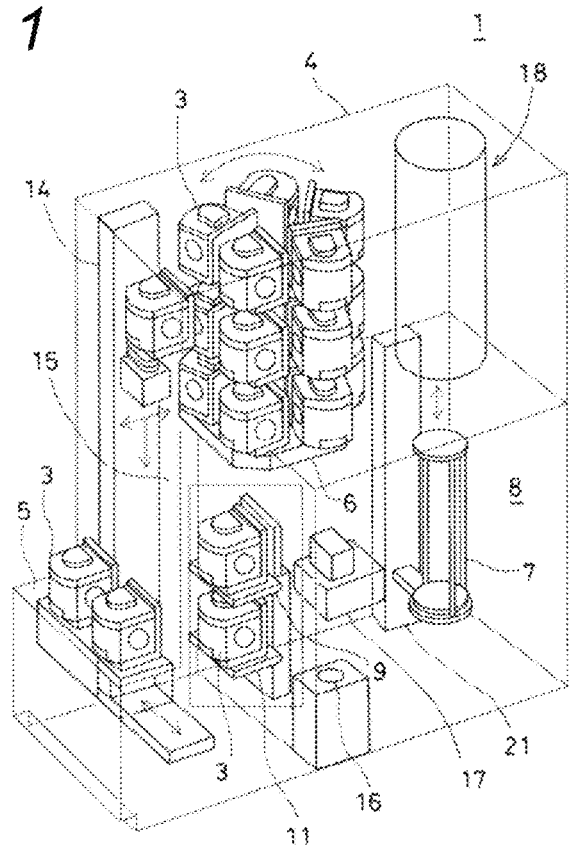
FIG. 1 is a perspective view illustrating a substrate processing apparatus according to an embodiment of the present invention.
Figure 2:
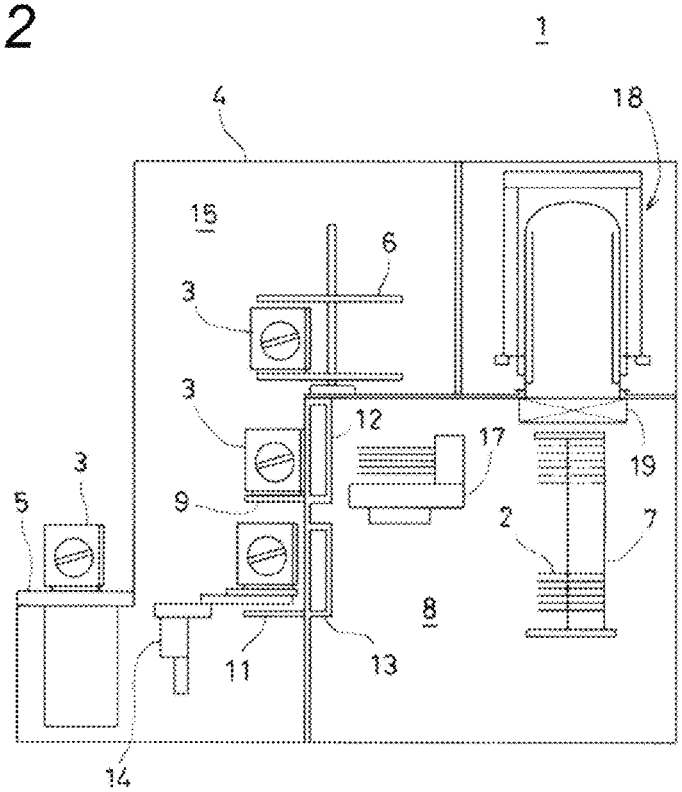
FIG. 2 is a cross-sectional view illustrating the substrate processing apparatus according to the embodiment of the present invention.

First, a substrate processing apparatus 1 according to an embodiment of the present invention will be described with reference to FIG. 1, FIG. 2.

Incidentally, in the following description, a case is described in which a vertical-type substrate processing apparatus is applied including a vertical-type furnace configured to perform diffusion treatment, CVD processing, and the like on a substrate as a substrate processing apparatus.

An I/O stage (substrate storage container exchanging unit) 5 is installed at a front of the housing 4, in order to load closed substrate storage containers (FOUP) (hereinafter referred to as cassettes 3) in which substrates such as wafers 2 formed of silicon and the like are accommodated, into a housing 4 from the outside and unload the cassettes 3 from the housing 4 to the outside, and a cassette shelf (storage means) 6 is installed in the housing 4 to store the loaded cassettes 3.

Also, an airtight chamber 8 is installed, being a transfer area of the wafers 2, serving as a loading or unloading space for a boat (substrate retaining mechanism) 7 described later. When the wafers 2 are processed, the inside of the airtight chamber 8 is filled with an inert gas, such as a N2 gas, to prevent a natural oxide film from being formed on the wafers 2.

A type of FOUP is currently used mainly as each of the cassettes 3, and the wafers 2 can be transferred while being isolated from the air by blocking an opening installed in one side surface of each of the cassettes 3 with a lid (not illustrated), and the wafers 2 can be loaded into or unloaded from each of the cassettes 3 by removing the lid. In order to communicate the inside of the cassette 3 with the airtight chamber 8 by removing the lid of the cassette 3, a plurality of sets (two sets in FIG. 1, FIG. 2) of cassette placing stages (substrate storage container placing means) 9, 11 is installed at a front side of the airtight chamber 8, and cassette openers 12, (opening/closing means) are installed on portions facing the cassette placing stages 9, 11 of the airtight chamber 8, respectively. The cassette openers 12, 13 can be driven individually, and the cassettes 3 placed on the cassette placing stages 9, 11 can be individually opened/closed.

The cassettes 3 are transferred among the cassette placing stages 9, 11, the cassette shelf 6, and the I/O stage 5 by a cassette transfer device 14 (carrier transfer unit). Cleaned air is caused to flow by a clean unit (not illustrated) installed in the housing 4, in a transfer space 15 in which the cassettes 3 are transferred by the cassette transfer device 14.

In the airtight chamber 8, the boat 7 in which a plurality of wafers 2 is stacked horizontally in multiple stages, and a substrate location adjustment apparatus 16 configured to adjust a position of a notch of the wafer 2 (or orientation flat) to an arbitrary position are installed, and also, a set of wafer transfer machine (substrate transfer units) 17 is installed configured to transfer the wafers 2 among the cassettes 3 on the cassette placing stages 9, 11, the substrate location adjustment apparatus 16, and the boat 7. Also, a process furnace 18 is installed for processing the wafers 2 on the airtight chamber 8, and a furnace port that is a lower end opening of the process furnace 18 is opened/closed by a furnace port gate valve 19. The boat 7 is loaded into the process furnace 18 or unloaded from the process furnace 18 by a boat elevator (elevating unit) 21 in an open state of the furnace port gate valve 19, and the furnace port gate valve 19 is closed during transfer of the wafers 2 to the boat 7.

Figure 3:
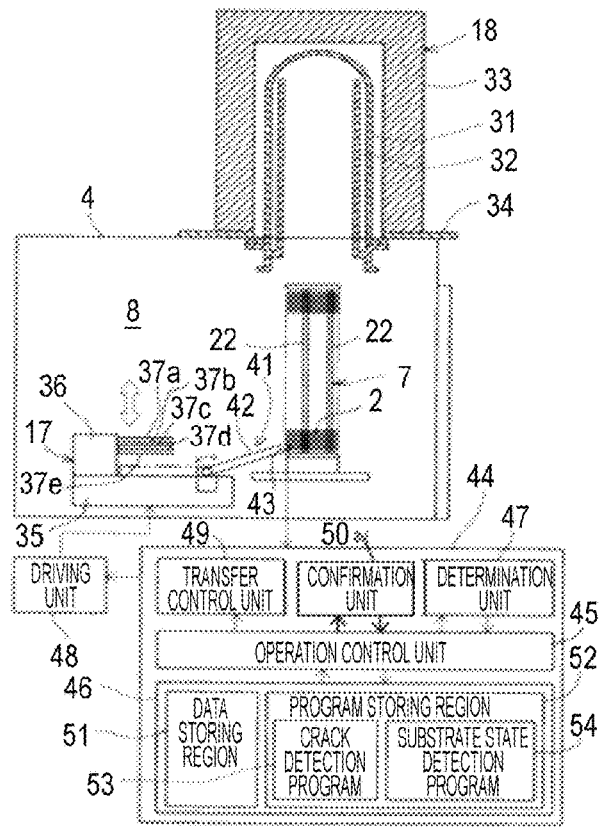
FIG. 3 is a cross-sectional view illustrating a process furnace and its peripherals used for the substrate processing apparatus according to the embodiment of the present invention.

FIG. 3 illustrates a peripheral configuration of the process furnace 18. The process furnace 18 includes an outer tube 31 formed of, for example, heat-resistant material, such as quartz (SiO2). The outer tube 31 has a cylindrical shape and has a ceiling, and, in the outer tube 31, an inner tube 32 having opened upper end and lower end is concentrically arranged. Also, a heater 33 as a heating means is concentrically arranged on an outer circumference of the outer tube 31, and the heater 33 is retained on the housing 4 through a heater base 34.

Next, processing of forming a film on the substrate as one step in a manufacturing process of a semiconductor device (device) using the substrate processing apparatus 1 described above (hereinafter referred to as deposition processing) will be briefly described below with reference to FIG. 3.

(Wafer Charge and Boat Load)

When the plurality of wafers 2 is charged into the boat 7 (wafer charge), the boat 7 is loaded into the process furnace 18 by the boat elevator 21 (boat load). At this time, a seal cap is in a state of airtightly closing (sealing) a lower end of the outer tube (hereinafter referred to as a reaction tube) 31 through an O ring. Incidentally, it is configured so that a wafer crack detection (or state detection) program described later is executed before the boat load.

(Pressure Adjustment and Temperature Adjustment)

Vacuum exhaust (decompression exhaust) is performed by a vacuum pump so that the inside of the process furnace 18, that is, a space in which the wafers 2 exist, has a predetermined pressure (degree of vacuum). At this time, the pressure in the process furnace 18 is measured by a pressure sensor, and feedback control is performed on an APC valve on the basis of the measured pressure information. The vacuum pump maintains a state of being operated at all times at least until the processing ends for the wafers 2.

In addition, heating is performed by the heater 33 so that the wafers 2 in the process furnace 18 have predetermined temperature. At this time, feedback control is performed on a current to the heater 33 on the basis of temperature information detected by a temperature sensor so that the process furnace 18 has a predetermined temperature distribution. Heating of the inside of the process furnace 18 by the heater 33 is continuously performed at least until the processing ends for the wafers 2. In addition, rotation of the boat 20 and the wafers 2 by a rotation mechanism is started. The boat 7 is rotated by the rotation mechanism, whereby the wafers 2 are rotated. The rotation of the boat 7 and the wafers 2 by the rotation mechanism is continuously performed at least until the processing ends for the wafers 2.

(Substrate Processing)

When the temperature in the process furnace 18 is stabilized at a processing temperature set beforehand, a predetermined gas is supplied to the wafers 2 in the process furnace 18, and predetermined processing is performed.

(Purge and Return to Atmospheric Pressure)

After the substrate processing is completed, the N2 gas is supplied into the process furnace 18, and is exhausted from an exhaust pipe. The N2 gas functions as a purge gas. Thus, the inside of the process furnace 18 is purged, and gases and reaction byproducts remaining in the process furnace 18 are removed from the inside of the process furnace 18 (purge). After that, the atmosphere in the process furnace 18 is replaced with an inert gas (inert gas replacement), and the pressure in the process furnace 18 is returned to normal pressure (return to atmospheric pressure).

(Boat Unload and Wafer Discharge)

The seal cap is lowered by the boat elevator 21, and the lower end of the reaction tube 31 is opened. Then, the processed wafers 2 is unloaded from the lower end of the reaction tube 31 to the outside of the reaction tube 31 in a state of being supported by the boat 7 (boat unload). The processed wafers 2 are taken out from the boat 7 (wafer discharge). Incidentally, it is configured so that the wafer crack detection (or state detection) program described later is executed after the boat unload.

In addition, the wafer crack detection (or state detection) program described later is preferably executed both before the boat load and after the boat unload. However, for operation of the substrate processing apparatus 1, execution of the wafer crack detection (or state detection) program described later can preferably be selected beforehand.

Figure 4:
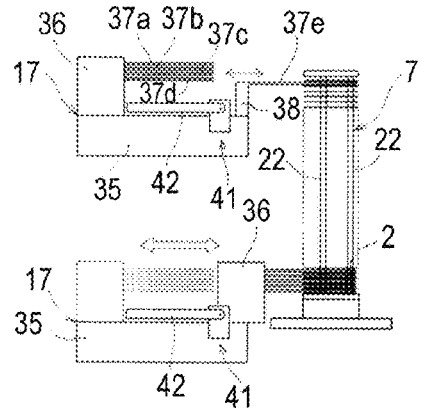
FIG. 4 is a side view illustrating a substrate transfer machine used for the substrate processing apparatus according to the embodiment of the present invention.

As also illustrated in FIG. 4, the boat 7 retains the wafers 2 with a retaining unit (also referred to as a slot). The wafer transfer machine 17 includes transfer machine body 35 that moves in the vertical direction and rotates, and a main tweezer body 36 that reciprocates on the transfer machine body 35. For example, four plate-like tweezers 37a, 37b, 37c, 37d are fixed to extend in parallel, to the main tweezer body 36. Also, a sub tweezer body 38 is installed to be capable of reciprocating together with the main tweezer body 36, and to be capable of reciprocating independently from the main tweezer body 36, on the transfer machine body 35. A tweezer 37e is fixed in parallel in the lower position of the four tweezers 37a-37d described above, to the sub tweezer body 38. For this reason, as illustrated in FIG. 4, the wafer transfer machine 17 is capable of collectively transferring five wafers 2 by the five tweezers 37a-37e, and also capable of transferring one monitor wafer by using the lowermost tweezer 37e (single wafer transfer). When the monitor wafer is transferred, a distance for one slot is spaced from the five wafers 2 collectively transferred, and the monitor wafer is taken out from the cassette 3 different from those of normal wafers 2, and inserted between five-wafer sets, as illustrated in FIG. 4.

when, for example, 25 wafers 2 are accommodated in the cassette 3 and the wafers 2 are transferred to the boat 7 or retrieve from the boat 7 by the wafer transfer machine 17, five wafers 2 are collectively transferred or retrieved by the five tweezers 37a-37e when there is no wafer 2 in a abnormal state among five retaining units (a slot group) on which the wafers 2 are placed, and only a wafer 2 in a normal state can be retrieved by using the tweezer 37e at the lowermost stage when there is a wafer 2 in an abnormal state among the slot group. Incidentally, the monitor wafer may be retrieved one by one similarly as in the case of insertion.

Figure 5:
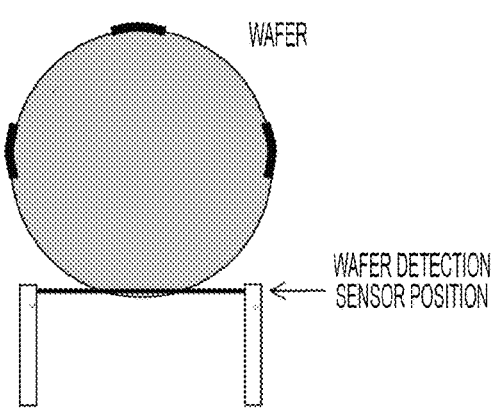
FIG. 5 is a plan view illustrating state detection by a detecting unit used for the substrate transfer machine according to the embodiment of the present invention.

A detecting unit 41 configured to detect the wafers 2 is installed on the transfer machine body 35. Also, as illustrated in FIG. 5, transmissive photo sensors 43a, 43b in which one is a light-emitting element and the other is a light-receiving element are installed to be arranged at a front side of the boat 7, and a state of the wafer 2 placed on the boat 7 is detected by the photo sensors 43a, 43b.

Also, when the state of the wafer 2 is detected, the optical axis of the photo sensors 43a, 43b is caused to pass through the wafer 2, and the wafer transfer machine 17 is moved from the lower end to upper end of the boat 7, and a detection output of the photo sensors 43a, 43b is monitored.

As illustrated in FIG. 3, an analog signal output from the photo sensors 43a, 43b is output to a control apparatus 44 embodied as, for example, a computer such as a PC. The control apparatus 44 includes: an operation control unit 45 such as CPU; a memory unit 46 including a memory and an HDD; a determination unit 47 configured to obtain a detection value described later by performing signal processing such as A/D conversion of data detected by the detecting unit 41, and comparing the detection value with data stored in the memory unit 46; and a transfer control unit 49 configured to control the wafer transfer machine 17 (substrate transfer unit) through a driving unit 48 including, for example, a motor, on the basis of a determination result by the determination unit 47.

The memory unit 46 includes a data storing region 51 and a program storing region 52, and the data storing region 51 stores various data such as master data described later. Also, the program storing region 52 stores a substrate state detection program 54 for performing state detection of the wafers 2 placed on the retaining unit by causing the determination unit 47 to compare the master data with the detection value. Incidentally, although not illustrated, various data and various programs for performing substrate processing on the wafers 2 are also stored in the data storing region 51 and the program storing region 52, respectively. In addition, the determination unit 47 includes a first determination unit 43a and a second determination unit 43b, as described later. In addition, the data storing region 51 stores wafer 2 information for each slot of the boat 7, and the confirmation unit 50 is configured to be capable of determining a wafer type on the basis of at least the wafer 2 information.

Figure 6:
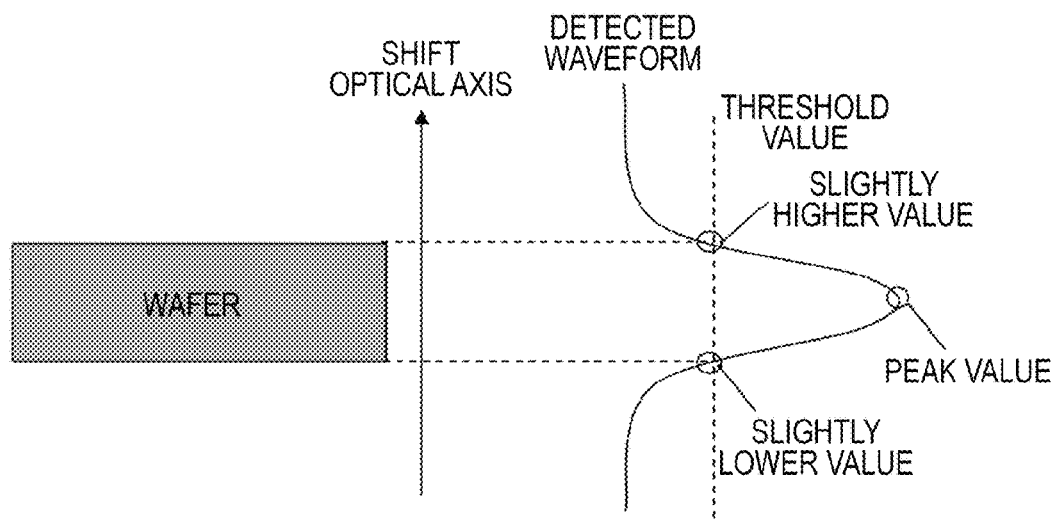
FIG. 6 is an explanatory diagram illustrating a case of detecting a product substrate by the detecting unit used for the substrate transfer machine according to the embodiment of the present invention.

First, obtaining of master data (first master data) for performing state detection of the wafer 2 will be described. The photo sensors 43a, 43b are moved from the bottom to the top in a state in which the wafers 2 are placed on the retaining unit of the boat 7, and waveform data (detected waveform data) as illustrated in FIG. 6 is obtained for each slot as the retaining unit, and is stored in the data storing region 51 in association with the slot. Also, the determination unit 47 obtains an amount of light of the lower end of the wafer, that is, a point in which the amount of light begins to decrease, as a lower wafer reference value (slightly lower value), obtains an amount of light of the upper end of the wafer 2, that is, a point in which the amount of light decreased is recovered, as an upper wafer reference value (slightly higher value), obtains an amount of light of the center of the wafer, that is, a point in which the amount of light is the largest, as the largest value of the waveform data (peak value), from each placed waveform data and stores the values in the data storing region 51. Incidentally, for obtaining actual master data, a substrate for substrate quality check called a monitor wafer or a new dummy wafer may be used, instead of the wafer 2 as a product substrate.

Next, the master data (first master data) is configured by wafer presence information, the lower wafer reference value, the upper wafer reference value, and the allowed wafer misalignment range (±an allowed value). Incidentally, although it looks like there is no width in each of the lower wafer reference value (slightly lower value) and the upper wafer reference value (slightly higher value) as illustrated in FIG. 6, an allowed value is set. That is, it illustrates that each of the values is as small as possible since misalignment of the wafers 2 has to be strictly checked.

Figure 7:
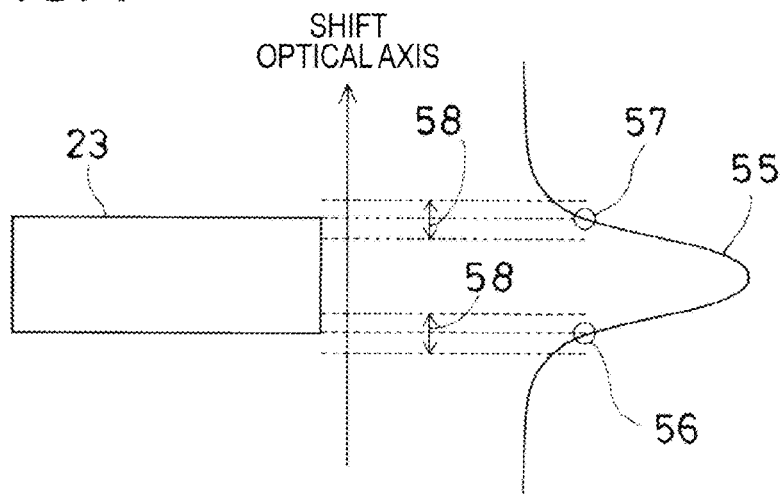
FIG. 7 is an explanatory diagram illustrating a case of detecting a dummy substrate placed on a retaining unit by the detecting unit used for the substrate transfer machine according to the embodiment of the present invention.

Next, obtaining of master data (second master data) for performing state detection of a dummy wafer 23 will be described. The photo sensors 43*a*, 43*b* are moved from the bottom to the top in a state in which the new dummy wafer 23 is placed on the retaining unit of the boat 7, and waveform data (placed waveform data) 55 as illustrated in FIG. 7 is obtained for each slot as the retaining unit, and is stored in the data storing region 51 in association with the slot. Also, the determination unit 47 obtains an amount of light of the lower end of the wafer, that is, a point in which the amount of light begins to decrease, as a lower wafer reference value 56, obtains an amount of light of the upper end of the wafer 2, that is, the amount of light decreased is recovered, as an upper wafer reference value 57, from each placed waveform data 55 and stores the values in the data storing region 51.

Also, a range in which the state of the dummy wafer 23 is regarded as normal, that is, an allowed range (±a target type allowed value) 58 of allowable misalignment is set, and stored in the data storing region 51. Here, the new dummy wafer is preferable for obtaining the master data, as described above. In addition, the value of the monitor wafer described above may be used as it is similarly for master data for performing state detection of the dummy wafer 23. Further, as for the lower wafer reference value 56, the upper wafer reference value 57, the setting may be changed depending on cumulative film thickness.

Then, master data to be used for state detection such as presence, crack, or falling of the wafer 2 and dummy wafer 23 is configured by wafer presence information, the lower wafer reference value 56, the upper wafer reference value 57, and the allowed wafer misalignment range 58, and the master data is stored in the data storing region 51 in association with the slot of each stage of the boat 7.

(Embodiment 1)

Figure 8:
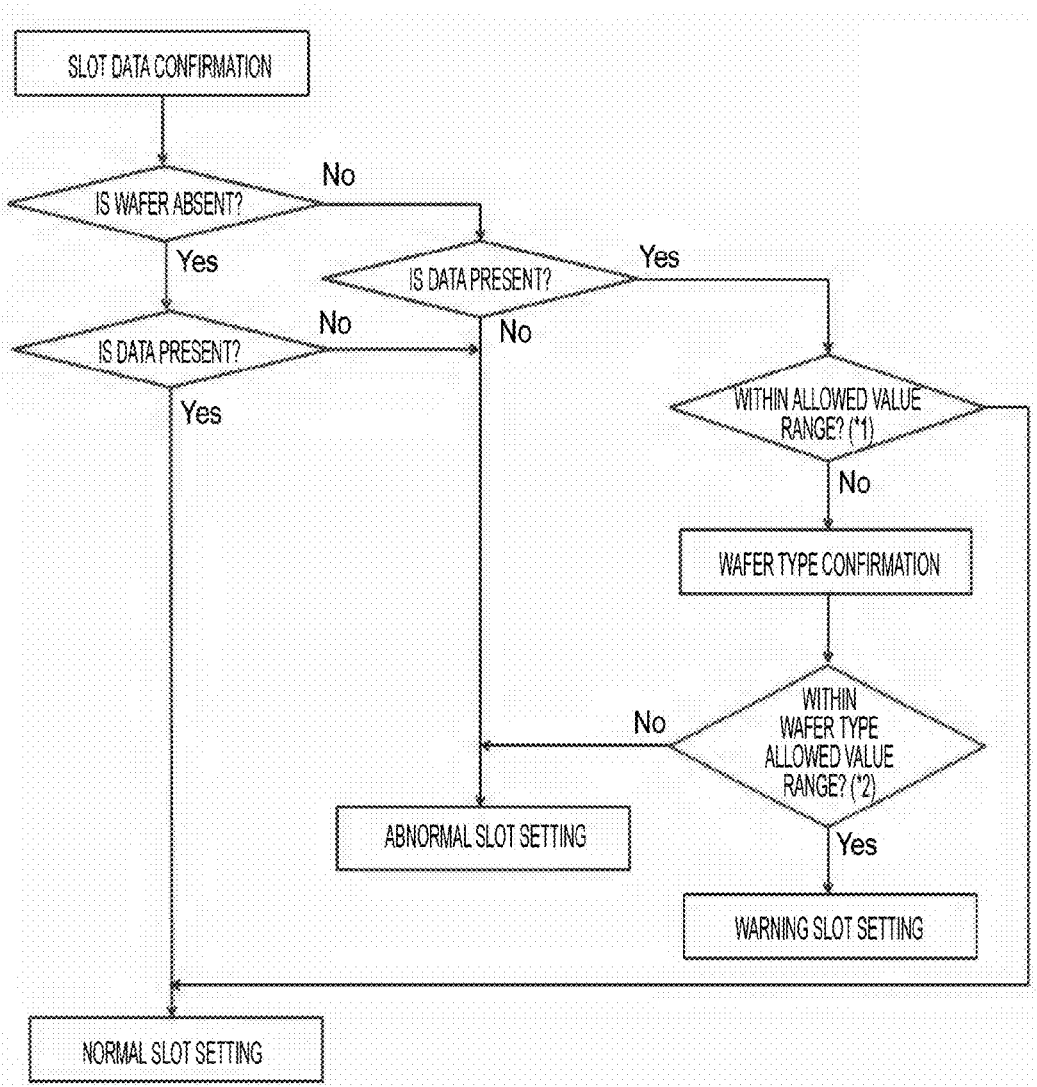
FIG. 8 is a flowchart describing state detection processing of a slot of a substrate retaining mechanism according to the embodiment of the present invention.
Figure 9:
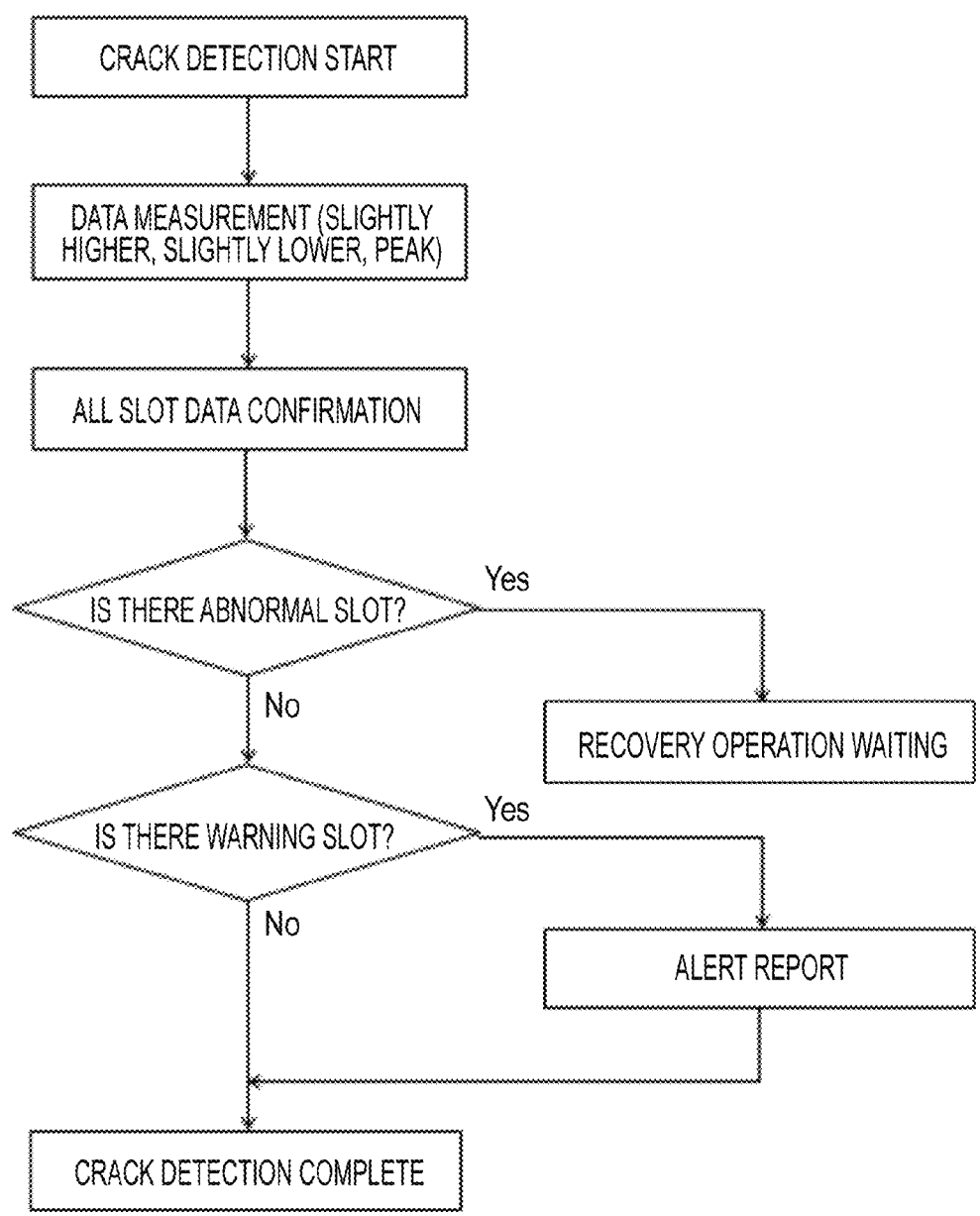
FIG. 9 is a flowchart describing crack detection processing of each slot of the substrate retaining mechanism according to the embodiment of the present invention.

Next, an embodiment (Embodiment 1) of the present invention will be described with reference to flowcharts of FIG. 8 and FIG. 9. FIG. 8 is a flowchart describing state detection processing of the slot of the substrate retaining mechanism according to the embodiment of the present invention. FIG. 9 is a flowchart describing crack detection processing of each slot of the substrate retaining mechanism according to the embodiment of the present invention. Incidentally, state detection processing of the slot and crack detection processing of each slot of the substrate retaining mechanism in the present embodiment are executed by the operation control unit 45 respectively with the substrate state detection program 54 and a crack detection program 53 stored in the program storing region 52.

The flowchart of FIG. 8 will be described. In FIG. 8, processing is performed of managing abnormality in the retaining unit (slot) of the boat 7. Specifically, it is determined whether the state of each slot of the boat 7 is set to normal, abnormal, or warning (alert).

As a first step, in a step (Step 1) of confirming presence of the wafer, when it is determined that wafer is absent (Yes), the step proceeds to a step (Step 2) of confirming presence of detection data, next. Then, when it is determined that the detection data is present (Yes), the target slot is determined as normal (normal slot setting) (Step 11). On the other hand, when it is determined that detection data is absent (No), the target slot is determined as abnormal (abnormal slot setting) (Step 12). In addition, when it is determined that a wafer is present (No) in Step 1, the step proceeds to a step (Step 3) of confirming presence of the detection data, next. Then, when it is determined that detection data is absent (No), the target slot is determined as abnormal (abnormal slot setting) (Step 12). On the other hand, when it is determined that the detection data is present (Yes), next, the step proceeds to a first determination step (Step 4) of comparing the detection data with the master data, and confirming whether or not there is wafer misalignment or distortion depending on whether or not the detection data is within a predetermined range.

In the first determination step (Step 4), it is determined whether or not the detection data is within a range of the master data±the allowed value. When the data is within a predetermined allowed value range (Yes), the target slot is set to a normal slot. On the other hand, when the detection data is not within the range of the master data±the allowed value (No), the step proceeds to a wafer type confirmation step (Step 5).

In the wafer type confirmation step (Step 5), a type of the substrate is confirmed. Incidentally, the step may be configured to be performed on only the substrate of a type other than product substrate. In addition, the step may be configured to be performed on only a case in which the type of the substrate is a dummy substrate. Then, when confirmation of the type of the substrate ends, the step proceeds to a second determination step (Step 6). In the present embodiment, since the allowed values can be changed with the dummy substrate, the monitor substrate, and the like, and is not the same value regardless of the substrate, here, it is determined whether or not detection data is within the range of the master data±substrate type allowed value by using the allowed value. For example, in a case of the dummy substrate, a range of the allowed value (first allowed value) to be used in the first determination step may be set narrower than the substrate type allowed value (second allowed value), and on the other hand, in a case of the monitor substrate, the range of the first allowed value may be set wider than the substrate type allowed value (second allowed value). The width (range) of the substrate type allowed value is larger than the allowed value, as can be easily understood from FIG. 6 and FIG. 7. This is to make it possible to use the dummy substrate without concerning to some misalignment, distortion, deflection, and the like, when the dummy substrate can be transferred. On the contrary, the second determination step is not necessarily had to be performed on the substrate other than the dummy substrate. Also in the second determination step (Step 6), when it is determined that the detection data is not within the range of the master data±substrate type allowed value (No), the target slot is set to an abnormal slot.

On the other hand, in the second determination step (Step 6), when it is determined that the detection data is within the range of the master data±substrate type allowed value (Yes), the target slot is determined as warning (warning slot setting) (Step 13). In addition, it is configured so that the steps of the flowchart are repeatedly performed on all slots to which the wafers 2 of the boat 7 are transferred.

Next, the flowchart of FIG. 9 will be described. In FIG. 9, processing is performed of managing crack detection abnormality of the wafer in the retaining unit (slot) of the boat 7. Specifically, as a result of determining whether the state of each slot of the boat 7 is set to normal, abnormal, or warning (alert), crack detection states of the wafers 2 placed on the retaining unit of the boat 7 are managed in the processing.

When a substrate crack detection program is started, data measurement (crack detection) is executed, and data is measured as illustrated in FIG. 6 (data detection) (Step 100). Then, the step proceeds to all slot data confirmation step (Step 101), and the steps of the flowchart illustrated in the FIG. 8 are repeated for all slots. After that, presence of the abnormal slot setting (Step 102) and presence of the warning slot setting (Step 103) are confirmed. When there is an abnormal slot, a recovery operation waiting step (Step 104) of removing abnormality is executed. In addition, when there is a warning slot, a target warning (alert) report step (Step 105) is executed. Incidentally, it is configured so that a signal indicating occurrence of an alert is notified, and the dummy substrate can be transferred to a slot set to the warning slot, in the alert report step (Step 105). By configuring in this way, timing of dummy replacement can be known in advance, by reporting an alert, even when the dummy substrate can be transferred to the target slot similarly to the normal slot.

In addition, according to the present embodiment, recovery operation waiting is not performed as much as possible, so that time of apparatus stop can be reduced.

In the embodiment (Embodiment 1) of the present invention, at least one or more effects of the following (a)-(e) are exerted.

(a) According to the embodiment of the present invention, abnormality detection can be determined in a different range for each wafer type in the wafer crack detection processing, and operation rate improvement can be achieved by continuing to use the dummy wafer when the dummy wafer can be transferred while monitoring the product wafer with a conventional reference, and extending a replacement cycle of the dummy wafer.

(b) According to the embodiment of the present invention, abnormality detection can be determined in a different range for each wafer type in the wafer crack detection processing, and the dummy wafer can be efficiently used, so that the dummy wafer can be used to the limit.

(c) In the embodiment of the present invention, the processing is suspended when there is abnormality such as a crack or deformation in the wafer 2, so that falling of the boat 7 and the like can be prevented caused by collision of the wafer 2 cracked or deformed and the tweezers 37a-37e. Further, in the embodiment of the present invention, the state of the wafer 2 can be detected, so that it is not necessary to add a mechanism separately for state detection of the wafer 2, and cost reduction can be achieved.

(d) According to the embodiment of the present invention, abnormality detection due to a minor deformation of the dummy substrate is suppressed, and the time of apparatus stop for recovery processing can be reduced. In addition, timing of replacement of the dummy substrate can be known in advance by warning (alert report).

(e) According to the embodiment of the present invention, excessive abnormality detection due to the dummy substrate is suppressed, and useless time of apparatus stop due to recovery operation waiting can be reduced, so that an increase of apparatus operation rate can be expected.

Incidentally, it is needless to say that the substrate processing apparatus 1 in the embodiment of the present invention can be applied to not only a semiconductor manufacturing apparatus but also an apparatus of processing a glass substrate such as an LCD device, and further can be applied to various apparatuses such as an exposure apparatus, a lithography apparatus, a coating apparatus, and a processing apparatus using plasma.

Further, as for deposition processing, the substrate processing apparatus can be implemented even in processing of forming a film containing metal, processing of forming an oxide film, nitride film, or processing of forming a thin film, such as CVD, PVD.

The present application claims the benefit of priority based on Japanese Patent Application No. 2014-154756 filed on Jul. 30, 2014, which is hereby incorporated by reference in its entirety.

INDUSTRIAL APPLICABILITY

The present invention can be applied to an apparatus configured to perform processing such as thin film formation, oxidation, impurity diffusion, and annealing, on a substrate (such as silicon wafer, glass substrate).

The invention claimed is:

1. A substrate processing apparatus comprising:
a substrate retaining mechanism retaining a substrate;
a detecting unit configured to detect a placed state of the substrate retained by the substrate retaining mechanism;
a first determination unit configured to compare detection data of the substrate obtained by the detecting unit with master data that is a reference and is obtained beforehand to determine whether or not the detection data of the substrate is within a first allowed value;
a confirmation unit configured to confirm a type of the substrate;
a second determination unit configured to compare the detection data of the substrate with the master data to determine whether or not the detection data is within a second allowed value; and
a transfer control unit configured to control the substrate retaining mechanism depending on a determination result of the second determination unit when it is confirmed that a type of the substrate is a predetermined type by the confirmation unit when it is determined that the detection data is not within the first allowed value as a determination result of the first determination unit, and
the transfer control unit makes a range of the second allowed value is being compared to the predetermined type.

2. The substrate processing apparatus according to claim 1,
wherein the substrate retaining mechanism is provided with a first predetermined number of retaining units each of which is configured to retain the substrate, and the transfer control unit is configured to repeatedly perform comparison by the first determination unit a first predetermined number of times, and repeatedly perform comparison by the second determination unit a second predetermined number of times.

3. The substrate processing apparatus according to claim 1,
wherein the transfer control unit is configured not to perform comparison by the second determination unit for each of the retaining units when a determination result of the first determination unit is that there is an abnormality, and a confirmation result by the confirmation unit is that the substrate is not of the predetermined type.

4. The substrate processing apparatus according to claim 1,
wherein, a range of the first allowed value is set narrower than that of the second allowed value in the comparison of the second determination unit when the confirmation result by the confirmation unit is that the substrate of the predetermined type is a dummy substrate.

5. The substrate processing apparatus according to claim 1,
wherein the transfer control unit is configured to set the range of the first allowed value to be same regardless of the type of the substrate.

6. The substrate processing apparatus according to claim 2,
wherein the transfer control unit confirms presence of substrate presence data and the detection data from the detecting unit for each of the retaining units, and sets the retaining unit in which there is not the substrate and there is the detection data, to abnormal slots.

7. The substrate processing apparatus according to claim 2,
wherein the substrate retaining mechanism is configured to wait until processing ends of removing an abnormality occurring in the retaining unit when the determination result of the second determination unit is that there is the abnormality.

8. The substrate processing apparatus according to claim 2,
wherein the transfer control unit is configured to set the range of the first allowed value to be same regardless of the type of the substrate.

9. The substrate processing apparatus according to claim 3,
wherein the transfer control unit is configured to set the range of the first allowed value to be same regardless of the type of the substrate.

10. The substrate processing apparatus according to claim 2,
wherein the first predetermined number is the number of all slots to which the substrate is transferred by the substrate retaining mechanism.

11. The substrate processing apparatus according to claim 1,
wherein, the range of the first allowed value is set wider than that of the second allowed value in the comparison of the second determination unit when the substrate of the predetermined type is a monitor substrate.

12. The substrate processing apparatus according to claim 2,
wherein the transfer control unit confirms presence of substrate presence data and the detection data from the detecting unit for each of the retaining units, and sets the retaining unit in which there is the substrate and there is not the detection data, to abnormal slots.

13. The substrate processing apparatus according to claim 1 wherein the predetermined type is a dummy substrate.

14. The substrate processing apparatus according to claim 1 wherein the predetermined type is a monitor substrate.

* * * * *